United States Patent [19]

Sagstetter et al.

[11] Patent Number: 5,092,462

[45] Date of Patent: *Mar. 3, 1992

[54] DISPOSAL FOR DISENGAGING AND RECEIVING NEEDLES

[75] Inventors: William E. Sagstetter, Denver; John E. Cooke, Lakewood, both of Colo.

[73] Assignee: Medical Safety Products, Inc., Denver, Colo.

[*] Notice: The portion of the term of this patent subsequent to Feb. 11, 2009 has been disclaimed.

[21] Appl. No.: 576,378

[22] Filed: Aug. 31, 1990

[51] Int. Cl.⁵ .................. B65D 85/24; B65D 83/10
[52] U.S. Cl. .................... 206/366; 604/192; 604/198
[58] Field of Search ............. 206/366, 365; 604/192, 604/198

[56] References Cited

U.S. PATENT DOCUMENTS

| | | | |
|---|---|---|---|
| 4,375,849 | 3/1983 | Hamifl | 206/366 |
| 4,466,538 | 8/1984 | Gianni | 206/366 |
| 4,494,652 | 1/1985 | Nelson et al. | 206/366 |
| 4,667,821 | 5/1987 | Shillington | 206/366 |
| 4,738,362 | 4/1988 | Barns et al. | 206/366 |
| 4,798,587 | 1/1989 | Willoughby | 604/110 |
| 4,801,013 | 1/1989 | Bruno | 206/366 |
| 4,802,579 | 2/1989 | Hall et al. | 206/366 |
| 4,807,344 | 2/1989 | Kelson et al. | 29/240 |
| 4,917,243 | 4/1990 | Abrams et al. | 206/365 |
| 4,986,811 | 1/1991 | Thead et al. | 604/219 |
| 4,995,871 | 2/1991 | Sasaki et al. | 604/219 |

Primary Examiner—William I. Price
Attorney, Agent, or Firm—Cahill, Sutton & Thomas

[57] ABSTRACT

A receptacle includes a first recess for receiving the anterior end of the barrel of a conventional double ended needle blood collection tube holder to stabilize the holder during threaded disengagement of the needle. A post is disposed within the recess to prevent rotation of the hub while the holder is rotated to unthread the hub. Upon threaded disengagement, the needle drops into the receptacle, which drop may be augmented by a pair of leaf springs. A second recess in the receptacle receives the collar of a guard supporting a translatable blood collection tube holder, which holder threadedly engages the hub of a double ended needle. A post within the recess can extend within the collar to engage a rib of the hub to prevent rotation of the double ended needle upon rotation of the guard to threadedly disengage the hub from the holder. Upon threaded disengagement, the double ended needle drops into the receptacle, which drop may be augmented by a pair of leaf springs.

21 Claims, 6 Drawing Sheets

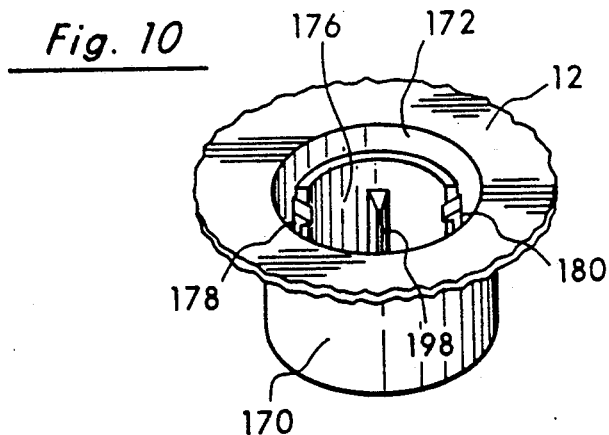
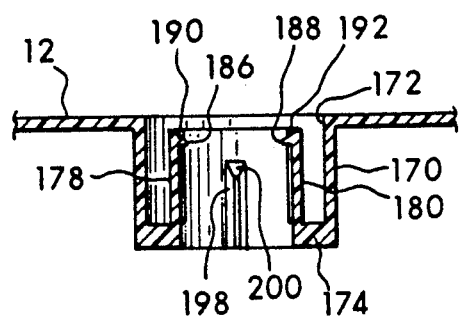
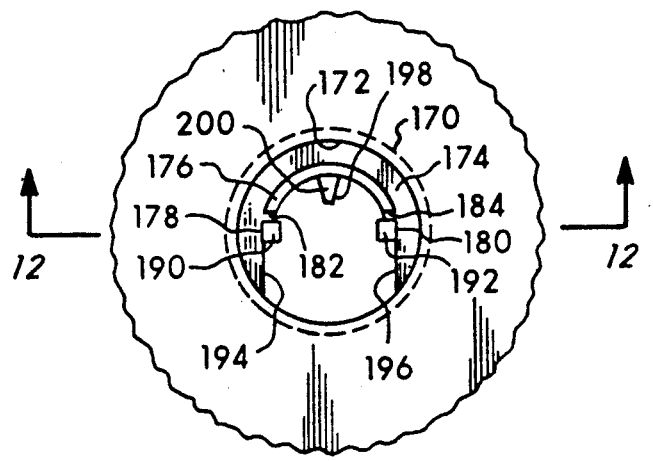

DISPOSAL FOR DISENGAGING AND RECEIVING NEEDLES

BACKGROUND OF THE INVENTION

1. Field of the Invention

The present invention relates to disposals and, more particularly, to disposals for needles and related devices.

2. Description of the Prior Art

To obtain a blood sample for diagnostic purposes, blood is drawn into an evacuated blood collection tube through a double ended needle. The needle includes a hub, an anterior needle for tissue penetration into a blood vessel and a posterior needle having an exterior elastomeric valve. The posterior end of the needle is penetrably inserted within a barrel having female threads for threadedly engaging the hub to retain the double ended needle positionally fixed with respect to the barrel. The proximal end of the barrel is open to receive an evacuated blood collection tube having a stopper for penetrably receiving the posterior needle. Upon venipuncture, blood will flow through the anterior needle and the posterior needle into the collection tube. Upon removal of the collection tube, the elastomeric valve recovers the posterior needle to prevent spontaneous blood flow from the needle. A phlebotomist can then insert a second or more blood collection tubes into the barrel to receive additional blood samples.

Upon completion of the venipuncture procedure, the anterior needle is withdrawn from the patient. While the barrel is often reused, the double ended needle must be safely removed from the barrel without causing needle stick and while avoiding contact with any residual body fluids of the patient to prevent transmission of infectious disease. Typically, a conventional biohazard receptacle for needles is provided with a lid having various shaped slots to engage the needle hub. To dispose of a used needle, the phlebotomist must carefully place the exposed needle hub into the slot, grip and rotate the barrel to unthread the needle and cause the disengaged needle to drop completely through the slot into the underlying container. Since the barrels are often opaque, it is difficult to know when the double ended needle has become completely threadedly disengaged from the barrel. A further danger arises from the upstanding exposed posterior needle until the hub has become sufficiently disengaged from the slot to permit the needle to drop into the receptacle. Aside from hub engaging slots, other devices have been developed including the use of fixed and moveable jaws to engage the needle hub. Mechanized devices for unthreading a double ended needle are also known.

A recently available reusable safety blood collection device includes a holder for engaging the double ended needle, which holder is translatable within a guard to fully enclose and shield both the anterior and posterior needles of the double ended needle. The guard includes an anterior collar for shielding the end of the anterior needle upon retraction of the holder and for supporting therewithin the hub engaging boss of the holder during use. Known syringe disposal devices are not well suited for receiving and disposing needles of such devices since the hub of the double ended needle is shielded by the collar and is not accessible for gripping by the opposed edges of a slot, jaws or the like.

SUMMARY OF THE INVENTION

A post mounted within a receptacle interferingly engages a rib of a conventional double ended needle hub to prevent rotation of the hub upon engagement of a rib. A sloping upper surface of the post encourages downward sliding movement of the needle into the receptacle upon threaded disengagement of the hub. In a second embodiment, a partial annular slot receives the collar of a guard for an enclosed double ended needle supporting holder and a post extending from the slot interferingly engages with a hub rib. Rotation of the guard with commensurate rotation of the enclosed holder will threadedly disengage the double ended needle from the holder whereafter the needle will drop into the receptacle. To encourage drop of the double ended needle, a pair of vertical diametrically opposed leaf springs may be incorporated, which leaf springs includes a lip for preventing upward withdrawal of the double ended needle. In a variant, the hub engaging and supporting post assembly along with a downwardly directed chute for guiding a double ended needle into a receptacle may be of modular construction attachable to an aperture of any container.

It is therefore a primary object of the present invention to provide apparatus for receiving and disengaging a double ended needle from a blood collection tube holder on completion of a venipuncture procedure.

Another object of the present invention is to provide a post for threadedly disengaging a double ended needle from a blood collection tube holder.

Still another object of the present invention is to provide a post for engaging a rib of the hub of a double ended needle to permit unthreading the needle from a blood collection tube holder in combination with a pair of leaf springs to encourage dropping of the needle into an underlying receptacle.

Yet another object of the present invention is to provide an annular slot for receiving a collar of a blood collection tube holder supporting guard, which collar is concentric with a post for interferingly engaging a rib of a double ended needle hub threadedly engaged with the holder.

A further object of the present invention is to provide a receptacle mounted post for engaging a rib of a double ended needle hub to permit threaded disengagement of the hub from a supporting blood collection tube holder and to encourage drop of the needle into the post supporting receptacle.

A still further object of the present invention is to provide a method for unthreading a used double ended needle prior to disposal.

A yet further object of the present invention is to provide a method for converting any receptacle to a disposal unit for double ended needles.

A yet further object of the present invention is to provide apparatus and method for safely disengaging a double ended needle from a blood collection holder while shielding a clinician from exposure to each end of the needle.

A yet further object of the present invention is to provide a transparent disposal for receiving a double ended needle from a transparent blood collection tube holder to permit visual inspection of the separation and disposal of the needle.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which:

FIG. 10 is a top isometric view of a further variant;

FIG. 11 is a top view of the further variant;

FIG. 12 is a cross sectional view taken along lines 12—12, as shown in FIG. 11.

DESCRIPTION OF THE PREFERRED EMBODIMENT

Receptacles for used blood collection tube holders with double ended needles of the type associated with venipuncture procedures have been in existence for a period of years. Such receptacles tend to reduce the likelihood of needle stick and spread of infectious diseases resulting from contact with the needles and body fluids disposed upon and within the needles. When blood collection tube holders used with the needles are not to be disposed, various problems arise in attempting to separate the double ended needle from the holder without requiring a phlebotomist to touch the needle. A number of devices for this purpose have been developed but each suffers from actual or potential problems which preclude repetitive fail safe operation.

Figure 1:
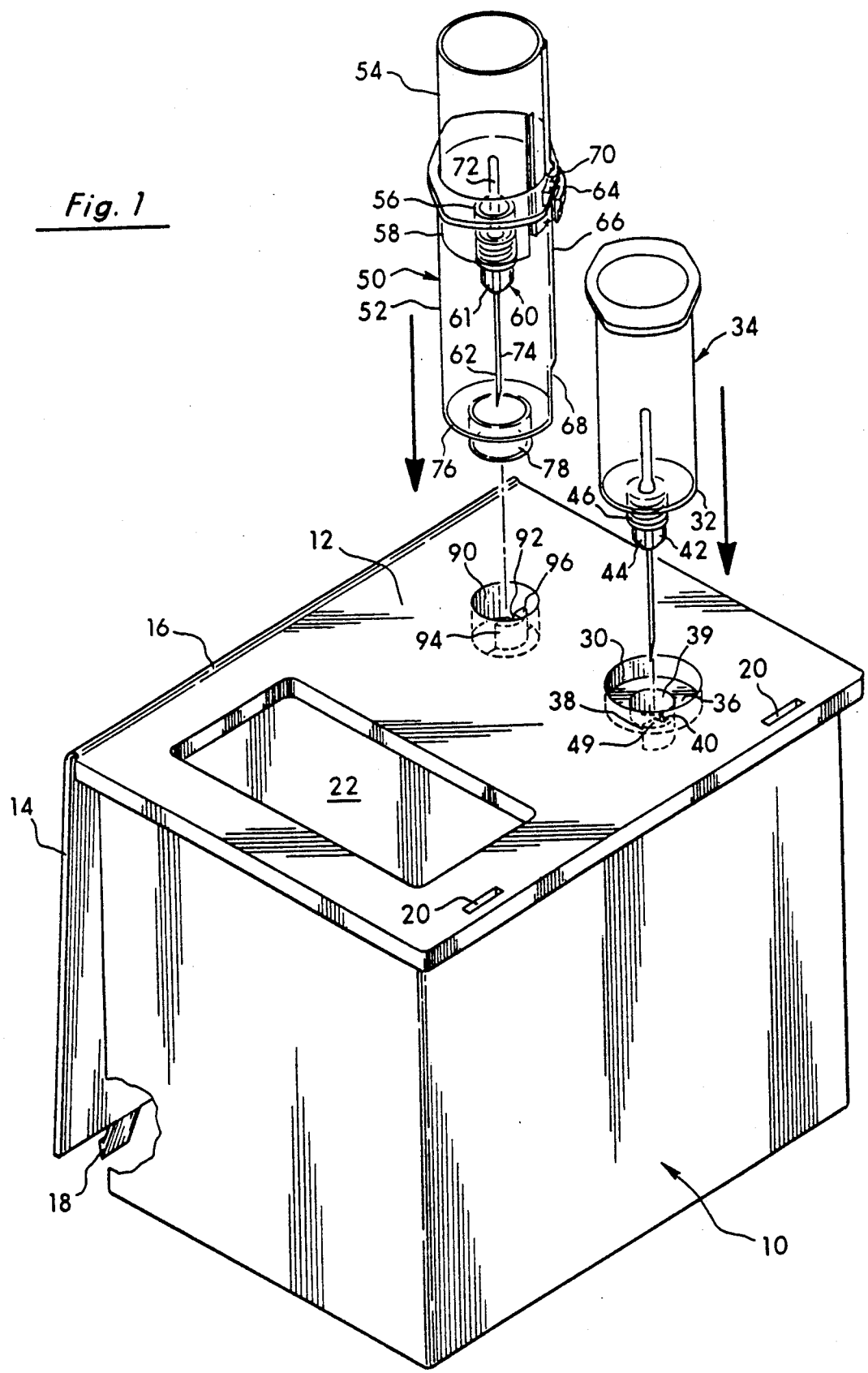
FIG. 1 is an isometric view of a container supporting posts for engaging the hubs of double ended needles threadedly engaged with different types of blood collection tube holders.

Referring to FIG. 1, there is illustrated a receptacle 10 for receiving and housing used double ended needles. The receptacle includes a top surface 12 and a cover 14. The cover may be hinged along hinge line 16. Prongs, such as prong 18 may extend from cover 14 for locking engagement with slots, such as slots 20 formed in top surface 12. An opening 22 may be formed in the top surface to permit insertion into the receptacle of various items for disposal.

Figure 2:
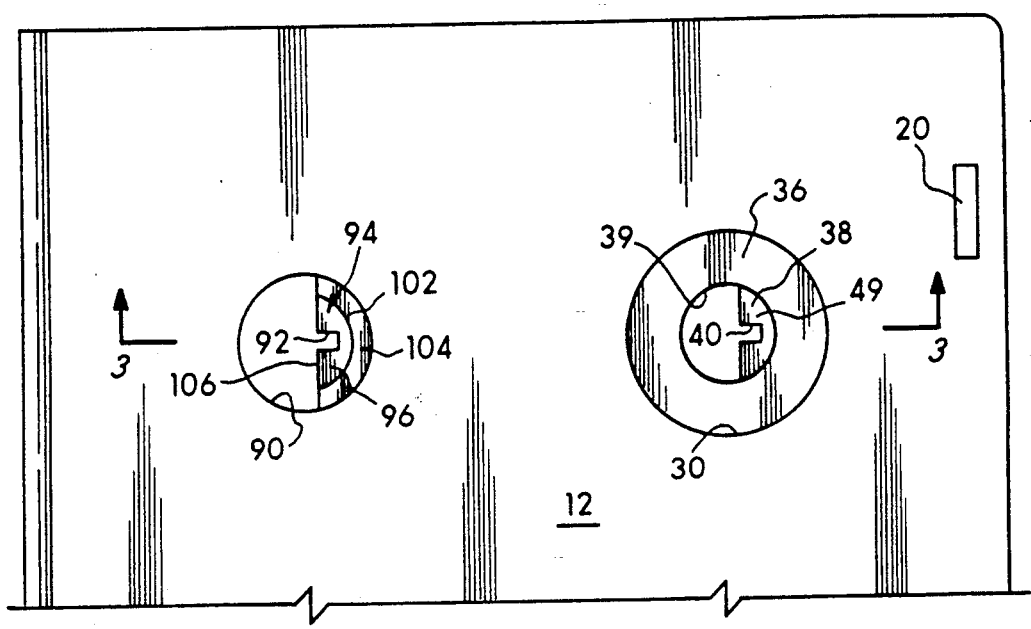
FIG. 2 is a partial top view of two types of post assemblies mounted in a container for receiving used doubled needles.
Figure 3:
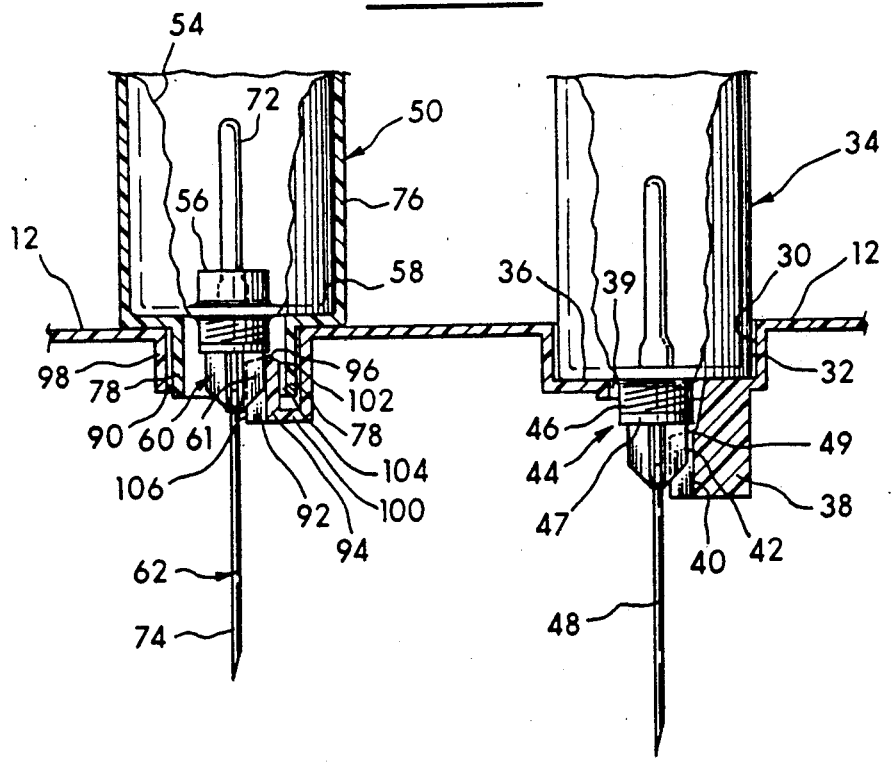
FIG. 3 is a partial sectional view illustrating the relationships between needle hub engaging devices and the respective types of blood collection tube holders.

Referring jointly to FIGS. 1, 2 and 3, a circular recess 30 is formed in top surface 12 to receive and nestingly support cylindrical anterior end 32 of a conventional blood collection tube holder 34. An apertured supporting surface 36, which may be partially or completely annular, is disposed at the bottom end of recess 30 to support anterior end 32 of the blood collection tube holder. A post 38, oriented off center within recess 30, includes a slot 40 for receiving a rib 42 formed in hub 44 of a conventional double ended needle threadedly engaged with boss 46 formed in anterior end 32 of the blood collection tube holder.

To eliminate the possibility of needle stick by phlebotomists during a conventional venipuncture procedure, a more complex blood collection tube holder device 50 has been developed. This device includes a barrel 52 for receiving and supporting a holder 54. The holder includes a boss 56 disposed at anterior end 58 for threadedly engaging hub 60 of a conventional double ended needle 62. A spring loaded tab 64 extends from anterior end 58 of holder 54 for penetrable engagement with and translation along a slot 66 formed longitudinally in barrel 52. Preferably, the slot includes laterally expanded anterior segment 68 and posterior segment 70 for lockingly receiving the tab to retain holder 54 locked in the anterior or posterior position. The axial length of holder 54 is sufficient to fully enclose posterior needle 72 to prevent inadvertent contact with the needle. Upon translation of holder 54 to its posterior position, anterior needle 74 is enclosed within the anterior portion of barrel 52. Anterior end 76 of barrel 52 includes a collar 78 for accommodating penetration therethrough of anterior needle 74 and at least a portion of hub 60 of double ended needle 62. Upon retraction of holder 54 to its posterior position, the end of anterior needle 74 may be located within the confines of collar 78.

To accommodate disengagement of double ended needle 62 from holder 54 on completion of a venipuncture procedure, receptacle 10 may be used. A cylindrical passageway 90 is sized and configured to receive and guide collar 78 through top surface 12 of the receptacle. The passageway also serves the function of stabilizing device 50 during the process of unthreading double ended needle 62 from holder 54. After placement of collar 78 within passageway 90, tab 64 is translated along slot 66 to position hub 60 within collar 78. Simultaneously, a rib 61 of the hub will slidingly engage slot 92 disposed in post 94 located within passageway 90. The size and orientation of post 94 permits the post to extend into collar 78 of device 50 to accommodate engagement with hub 60.

To disengage the double ended needle from blood collection tube holder 34, the holder is inserted into recess 30, guiding the anterior needle 48 through aperture 39 downwardly into adjacent slot 40 until rib 42 of hub 44 slidingly engages the slot. In this position, anterior end 34 of the holder will rest upon and be supported by supporting surface 36. Upon counterclockwise rotation of the holder, commensurate rotation of hub 44 will be precluded by interference between rib 42 and slot 40, resulting in unthreading of the hub from the holder. Upon subsequent raising of the holder out of the recess, the hub, will slide downwardly into the receptacle through the space between post 38 and supporting surface 36. Such downward sliding movement is encouraged if top surface 49 of the post is canted downwardly toward slot 40.

To separate double ended needle 62 from holder 54 of device 50, collar 78 is inserted within passageway 90 until anterior end 76 of barrel 52 rests upon top surface 12 of receptacle 10. Thereafter, tab 64 is brought out of detent or expanded segment 70 and translated along passageway 66 until rib 61 of hub 60 engages slot 92 in post 94. Subsequent counterclockwise rotation of barrel 52 will result in commensurate rotation of holder 54 due to interference therebetween provided by tab 64 and slot 66 or further detent or expanded segment 68. The counterclockwise movement will unthread hub 60 from boss 56. Prior to or upon lifting of device 50, disengaged double ended needle 62 will drop through the space intermediate post 94 and passageway 90. Downward sliding movement of the double ended needle will be enhanced if top surface 96 of post 94 cants downwardly toward the slot.

Referring jointly to FIGS. 2 and 3, further details attendant the needle receiving elements of receptacle 10 will be described. Post 38 attendant recess 30 depends from a segment of supporting surface 36. By incorporating recess 30, anterior end 32 of holder 34 is reasonably well guided and supported during rotation of the holder to prevent skewing of the double ended needle upon partial unthreading and the act of unthreading will be enhanced. Moreover, the recess will maintain the holder in axial alignment with slot 40 to ensure continuing engagement of rib 42 of the hub with the slot. Top surface 49 of post 38 is necessarily dropped below supporting surface 36 to an extent sufficient to accommodate the extending axial dimension of boss 46 and the axial positioning of a band 47 normally found in hub 44, which band segregates the ribbed portion of the hub from the threaded portion of the hub. As noted above, a downward canting of top surface 49 is preferable to encourage sideways movement of a freed double ended needle to assist the hub in clearing the post prior to dropping into receptacle 10. As particularly noted in FIG. 2, post 38 may extend across a chord of aperture 39 defined by supporting surface 36. Such configuration will assist in locating the hub of the needle with respect to slot 40 and minimize the likelihood of the hub missing or not engaging the post in the manner intended.

Passageway 90 includes and is defined by a depending annular skirt 98, which skirt guides and stabilizes collar 78 upon mounting of device 52. A shelf 100 extends centrally into passageway 90 from skirt 98, which shelf supports post 94. The post may include a curved side 102 concentric with passageway 90 to define therebetween an annular slot 104 for receiving a segment of collar 78 of device 50. Slot 92 may extend inwardly from a flat surface 106 interconnecting opposed edges of curved side 102.

As will be evident by inspection, annular slot 104 in combination with the remaining surface area of skirt 98 defining passageway 90 will permit unimpeded rotation of device 50 about its longitudinal axis (and double ended needle 62) but generally impede pivoting or lateral displacement of the device. The limited permissible movement of the device will encourage non binding interference between the rib engaged with slot 92 and permit ready disengagement upon dropping of the double ended needle after threaded disconnection between hub 60 and boss 56.

Figure 4:
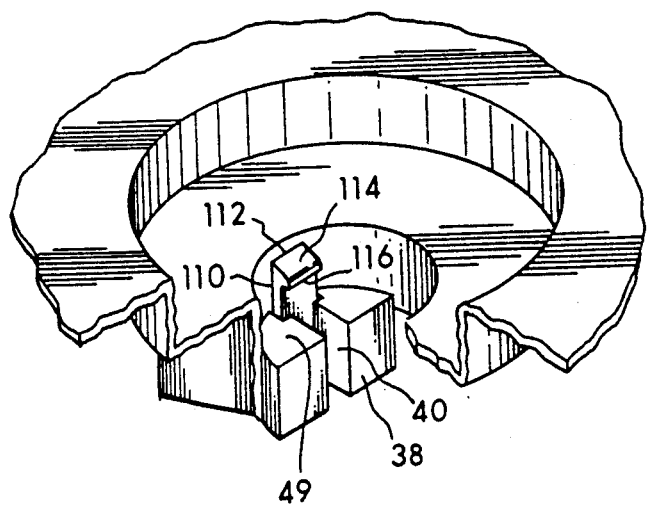
FIG. 4 illustrates a variant of the hub engaging post structure.

Referring to FIG. 4 there is shown a variant structure for either or each of posts 38, 94. Under abnormal conditions, a double ended needle may not disengage from the supporting post and drop into receptacle 10 as intended and expected. To encourage lateral movement of the hub of the respective double ended needle off of the top surface of the respective post and to totally eliminate any basis for support for the double ended needle, bias means may be incorporated to force the needle out of engagement with the post. A bias means of this type is illustrated in FIG. 4. A leaf spring 110 is disposed at the rear of a slot, such as slot 40, of one of the posts, such as post 38. This leaf spring may be formed as part of the post with its lower end extending upwardly from the lower part of the post. As illustrated, the leaf spring may replace the wall portion of the post directly rearwardly of the respective slot; the leaf spring may be formed in place of a part of the wall portion depicted in FIGS. 2 and 3; or, the leaf spring may be separate from the post. By having leaf spring 110 extend forwardly in its relaxed state, it will be forced rearwardly upon engagement of a double ended needle hub with the post. Accordingly, the leaf spring will bear against and bias the hub out of the slot. Upon disengagement of the double ended needle from the blood collection tube holder, the double ended needle will no longer be positionally restrained and the bias urged by the leaf spring will be exercised. Such exercise will cause the double ended needle to be urged out of engagement with the slot. Leaf spring 110 thereby contributes to release of the double ended needle to permit it to drop under force of gravity into the underlying receptacle; the drop may be augmented by the leaf spring. As depicted in FIG. 4, top surface 49 may be canted to further encourage disengagement between the double ended needle and the post.

Conventional double ended needles include a band disposed about the hub intermediate the threaded segment and the ribbed segment, as illustrated in FIG. 3. Under certain circumstances, despite threaded disengagement between a blood collection tube holder and a double ended needle, the double ended needle may remain attached to the boss of the blood collection tube holder. Upon withdrawal of the blood collection tube holder, the double ended needle may inadvertently be withdrawn from receptacle 10 and later drop somewhere else. To prevent this from happening, leaf spring 110, as shown in FIG. 4, includes a lip 112 for bearing against the upper edge of the band attendant the hub of the double ended needle. Because of the bias provided by the leaf spring, the lip will be urged toward the hub for such engagement. To permit passage of the band past the lip upon insertion of the double ended needle, a ramp 114 may be formed to force the lip laterally as the band passes therepast. The resulting sharp edge 116 will assist repositioning of the lip adjacent the top edge of the band of the hub upon initial unthreading of the hub. Upon upward movement of the holder due to threaded release of the double ended needle, the lip, bearing against the upper edge of the band about the hub, will then move over the top surface of the band and restrain upward movement of the double ended needle. Such restraint will be enough to completely disengage the needle from the blood collection tube holder. Once complete disengagement is effected and with the aid of the leaf spring mounted lip, the double ended needle is free to drop into the receptacle, as discussed above.

Figure 5:
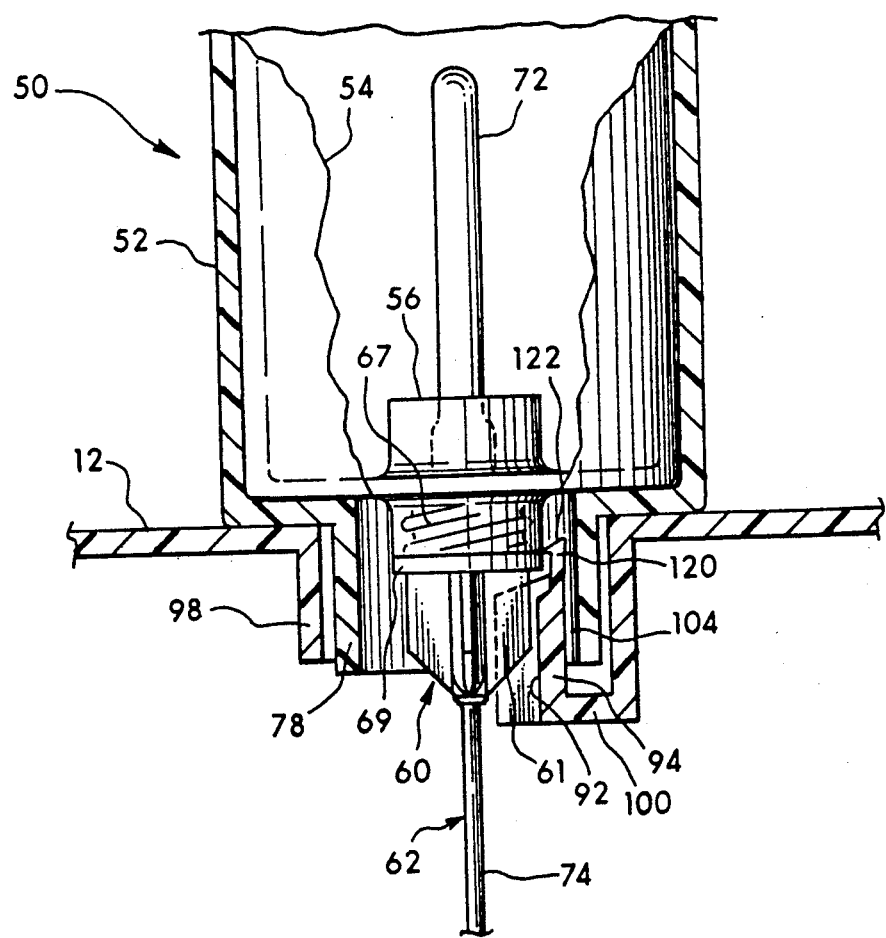
FIG. 5 is a partial cross sectional view illustrating operation of the variant shown in FIG. 4.
Figure 6:
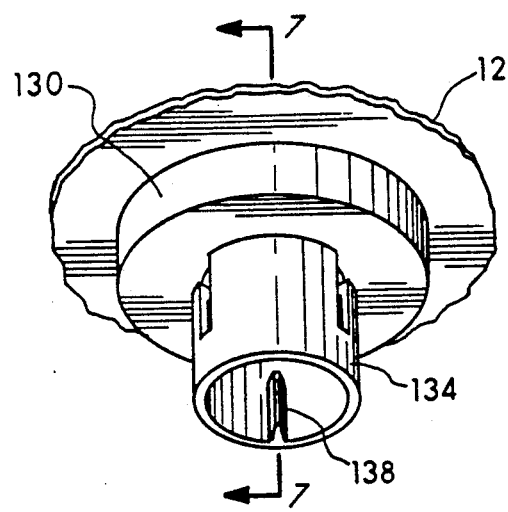
FIG. 6 is an isometric view of a variant of the needle hub engaging post and associated structure.
Figure 8:
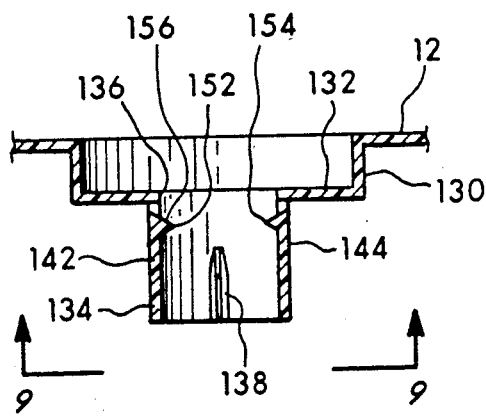
FIG. 8 is a cross sectional view taken along lines 8—8, as shown in FIG. 7.
Figure 7:
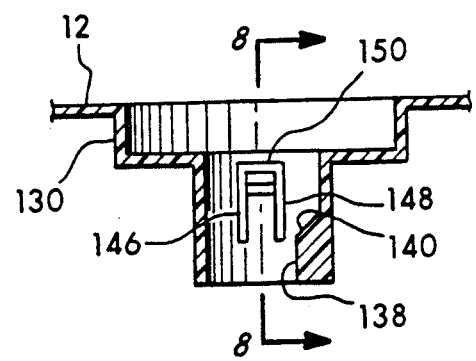
FIG. 7 is a cross sectional view taken along lines 7—7, as shown in FIG. 6.
Figure 9:
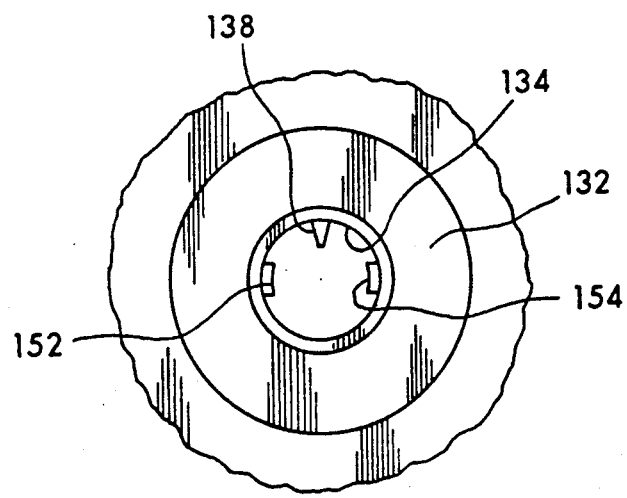
FIG. 9 is a bottom view taken along lines 9—9, as shown in FIG. 8.

A further structural configuration of leaf spring 110 with its lip 122 is depicted in FIG. 5. Post 94, as also shown in FIG. 3, includes a slot 92 for receiving rib 61 of hub 60 in threaded engagement with boss 56 of device 50. The hub includes an annular band 69 disposed intermediate the plurality of ribs and threaded segment 67. Bias means, which may be a leaf spring 120, extends upwardly from post 94 laterally of slot 92. The upper end of the leaf spring includes a lip 122 extending from the leaf spring toward the slot. The vertical position of lip 122 is set to permit band 69 to be placed intermediate the top of post 94 and the lip. Furthermore, the orientation of the leaf spring, in combination with the extent of lip 122, is established to ensure overlap of the lip with the band upon engagement of hub 60 with post 94. Upon such initial engagement, the band may cause the leaf spring to spring rearwardly (laterally) to permit the band to clear the lip. Upon further downward movement of the band, the leaf spring will cause the lip to translate forwardly (laterally) into an overlying engagement with the band. Subsequent upward movement of hub 60 would result in interference between band 69 and lip 122 to discourage further upward movement. Thereby, lip 122 in combination with its supporting leaf spring 120, will encourage complete disengagement between double ended needle 62 and boss 56. Alternatively, a single bendable lip or lips may extend radially inwardly to engage the hub and prevent withdrawal of the needle.

Referring jointly to FIGS. 6, 7, 8 and 9, a cylindrical wall 130 depends from top surface 12 to define a cylindrical recess for receiving end 32 of a blood collection tube holder, such as holder 34 shown in FIG. 1. An annular base 132 extends radially inwardly from the cylindrical wall to support the holder. A cylindrical skirt 134 depends from the annular base proximate aperture 136 formed centrally of the annular base. The interior diameter defined by cylindrical wall 130 is approximately equivalent to that of end 32 of the blood collection tub holder. The interior diameter of cylindrical skirt 134 is approximately that defined by hub 44 (see FIG. 1) double ended needle 62. As discussed above, hub 44 includes a plurality of ribs, usually equiangularly spaced, extending longitudinally along the hub. A longitudinally oriented post 138 extends radially inwardly from cylindrical skirt 134. The extent of radial inward extension of post 138 is sufficient to interferingly engage with one of the ribs on hub 44 upon insertion of end 32 of the blood collection tube holder within the recess defined by cylindrical wall 130. Thus, post 138 will interferingly engage a rib of the hub to prevent rotation of the hub commensurate with rotation of the holder; thereby, threaded disengagement of the hub from the holder may be effected.

To encourage drop of double ended needle 62 (FIG. 1) into receptacle 10 upon threaded disengagement with the holder, the end of the post may be canted inwardly downwardly to serve in the manner of a ramp 140 to encourage downward sliding movement of the double ended needle.

Sometimes, due to manufacturing tolerances or for other reasons, disengagement between the double ended needle and the holder may require application of a force more positive than that of gravity. To ensure disengagement after unthreading, a pair of diametrically opposed leaf springs 142,144 may be formed in cylindrical skirt 134. These leaf springs may be defined by a pair of slots 146,148 joined at the upper end by a third slot 150. Thus, the lower end of each leaf spring is formed as a part of the cylindrical skirt while the upper end is free to flex. The interior upper end of leaf spring 142 includes an inwardly directed lip 152. The radial inward extension of lip 152 is sufficient to engage the top edge of the needle hub and interfere with upward withdrawal of the hub upon upward movement of the holder. Leaf spring 144 includes a similar lip 154. Upper surfaces 156,158 may be canted inwardly downwardly to accommodate passage therepast of the hub upon insertion of the blood collection tube holder within cylindrical wall 130. During such insertion, the leaf springs will cant radially outwardly to accommodate transport of the hub past lips 152,154.

Referring jointly to FIGS. 10, 11 and 12, there is shown a further variant for receiving a more complex blood collection tube holder device 50, as shown in FIG. 1. A cylindrical wall 170 extends downwardly from top surface 12 and defines an aperture 172. A base 174 extends radially inwardly from a part of the lower end of the cylindrical wall. In particular, the base defines a semi annular segment for supporting an upwardly extending semi cylindrical flange 176. The flange is radially inwardly displaced from the interior surface of cylindrical wall 172 to form a slot having a radial width commensurate with the radial width of collar 78 of blood collection tube device 50 (see FIGS. 1 and 3). The longitudinal extremities of the semi cylindrical flange include leaf springs 178,180. These leaf springs may be formed as part of the semi cylindrical flange and defined by slots 182,184. The upper ends of the leaf springs may include radially inwardly oriented lips 186,188. The top of these lips may be canted downwardly inwardly to define ramps 190,192. Base 174 may be terminated by edges 194,196, which edges extend tangentially from leaf springs 178,180 to cylindrical wall 170. A post 198 extends radially inwardly from semi cylindrical flange 176 at its approximate mid point. The upper end of the post may be canted inwardly downwardly to define a ramp 200.

In operation, collar 78 (see FIG. 3) of blood collection holder device 50 is inserted within the slot defined by cylindrical wall 170 and semi cylindrical flange 176. Support for the blood collection tube holder device may be provided by the holder resting on surface 12 and by collar 78 resting upon base 174 or either one. The inward extension of post 198 is sufficient to extend adjacent the body of hub 60 and intermediate ribs 61 of the hub to interferingly engage a rib in the event of rotation of the blood collection tube device about its longitudinal axis. Thereby, rotation of the blood collection tube device will result in unthreading and disengagement of the hub supported double ended needle from the blood collection tube device. Upon withdrawal of the blood collection tube device, the hub and its needle will drop into receptacle 10. To ensure disengagement of the hub, lips 186,188 of leaf springs 178,180 are vertically positioned and radially inwardly extended to contact the upper end of the hub. With such contact, a resistive force will be exerted upon the hub to prevent upward translation of the hub in response to upward movement of the blood collection tube device. Thereby, disengagement of the hub supporting needle will be assured. By forming ramp 200 upon the post, the upper end of the post will have little support for the hub and the hub will slide off the post. By forming the upper surfaces of leaf springs 186,188 with ramps 190,192, lateral outward displacement of the leaf springs to accommodate downward passage therepast of the hub is assured.

By inspection, it will be evident that the retention and positioning of the collar of the blood collection tube holder device intermediate semi cylindrical flange 176 and the interior wall of cylindrical wall 172, little lateral movement of the blood collection tube holder device will result; thus, interfering engagement by post 198 with the ribs of the hub is assured.

Figure 13:
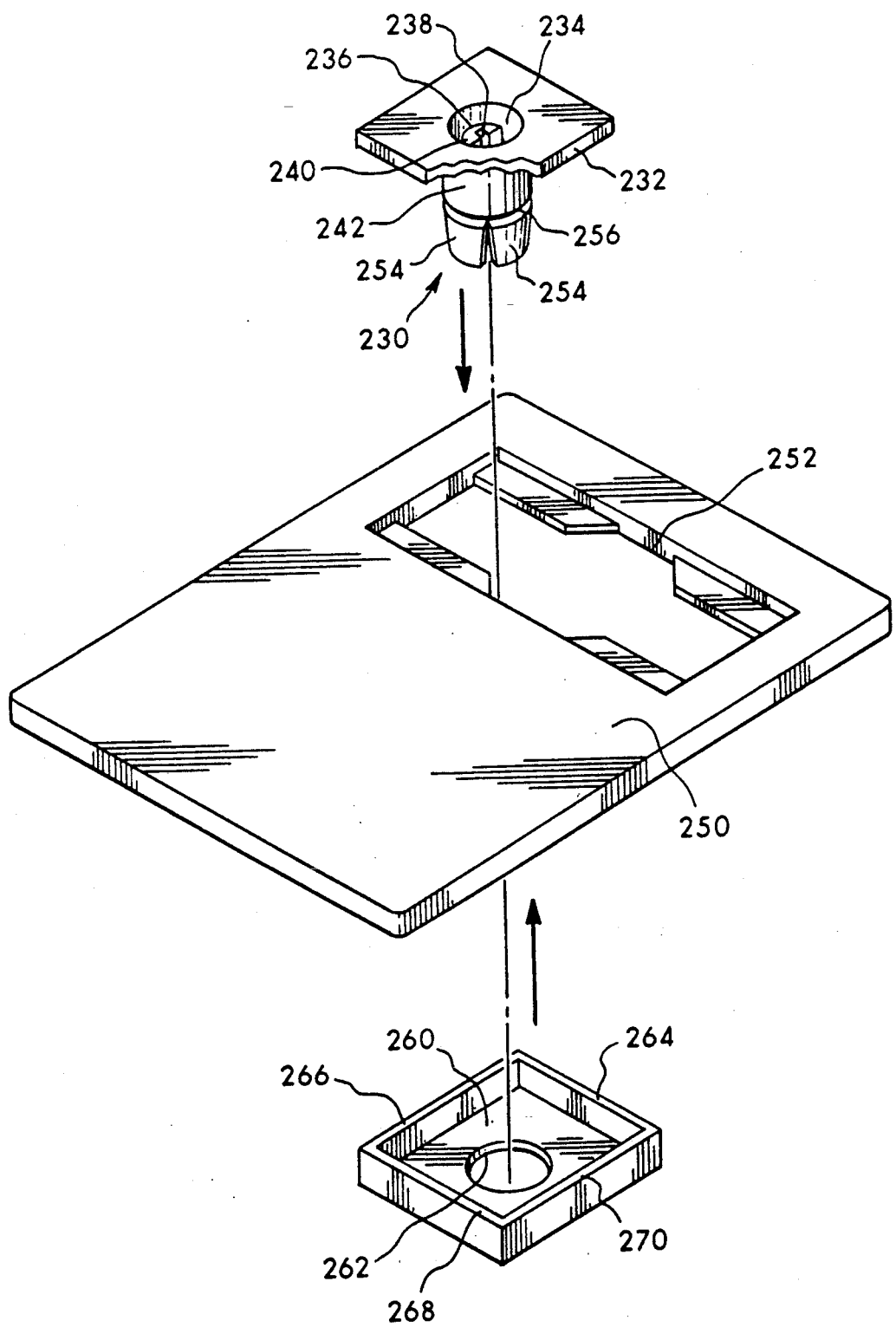
FIG. 13 is an exploded view illustrating a yet further variant of the present invention and mounting means therefor.

FIG. 13 illustrates a variant of the present invention usable in conjunction with any container or receptacle having a lid, which receptacle is to be employed for receiving used double ended needles. A module 210 includes a plate 212 having a recess 214 formed therein; this recess may be of the type shown in FIG. 3 for use with a blood collection tube holder 34 or for use with a blood collection device 50 or of the type shown in either of FIGS. 6 or 10. As described above, a post 236 having a slot 238 is disposed within recess 234. Top surface 240 of post 236 may be horizontal, as depicted, or may be canted, as shown in FIG. 3; alternatively, the post may be of the type described with respect to FIGS. 6 to 10. A circular shroud 242 extends downwardly from plate 232. This shroud serves in the manner of a guide or chute to direct disengaged double ended needles therethrough.

Module 230 is to be used in conjunction with a receptacle having an apertured top for penetrably receiving shroud 242. Thereby, any receptacle can be used as a disposal unit for double ended needles upon attachment of module 230. The means for retaining the module in place may be permanent or temporary.

A top 250 of a presently widely used receptacle is depicted. The top includes an aperture 252 of sufficient size to permit penetrable engagement by shroud 242. The length and width of plate 232 supports module 230 upon top 250 after penetration of shroud 242. The lower end of the shroud may include a plurality of outwardly biased resilient wings 254 extending downwardly from a groove 256 formed in the shroud. Locking means, such as plate 260, includes an aperture 262 dimensioned to be seated in groove 256.

In operation, module 230 is penetrably engaged with aperture 252 of top 250. Protruding wings 254 are forced radially inwardly to pass through aperture 262 in plate 260 and the plate is translated upwardly along shroud 242 until aperture 262 seats within groove 256. Thereafter, wings 254 will tend to spread radially outwardly to prevent disengagement of plate 260. The module will now be locked in place. Plate 260 may include upwardly extending sidewalls 264,266,268 and 270 to provide dimensional correspondence between the extent to which groove 256 is below top 250 with the position of aperture 262 of plate 260 to preclude vertical movement of the module and to frictionally maintain the module at a predetermined location within aperture 252.

Even though top 250 having a particularly configured aperture 252 corresponds with a widely used type of receptacle, it is to be understood that module 260 may be used with any receptacle having an aperture sufficient in size to penetrably receive shroud 242 and permit locking the module in place with a plate, such as plate 260.

Blood collection holder device 50, illustrated in FIGS. 1, 3 and 5, was developed by Medical Safety Products, Inc. for the purpose of eliminating exposure of both the anterior and posterior needles of a double ended needle while handling of the holder other than during the venipuncture procedure itself. That is, after attachment of a conventional double ended needle, the device may be immediately used for venipuncture; alternatively, the double ended needle may be retracted within the guard of the device in the event there will be a time lapse prior to use. After withdrawal of the needle on completion of a venipuncture procedure, the anterior needle is retracted within the guard to prevent needle stick and to contain any body fluids of the patient which may be on or about the needle. Prior to retraction, the posterior needle is shielded by both the holder and the guard. Upon retraction of the double ended needle, the posterior needle remains shielded within the holder to prevent needle stick or contact therewith by a clinician. Passageway 90 (FIG. 3) or the slot adjacent cylindrical wall 170 (FIG. 10) receives the collar extending anteriorly from the barrel, which collar may partly house and shield the end of the anterior needle. Prior to and during the act of mating the collar with the passageway or the slot, the anterior needle remains shielded and accidental contact therewith by a clinician will be precluded. During extension of the double ended needle prior to segregation of the needle from the holder, the anterior needle is interior of receptacle 10 (FIG. 1), which receptacle shields the needle against accidental contact by the clinician. After unthreading of the double ended needle from the holder, the needle will drop into the receptacle with little possibility that the clinician can contact either the anterior or posterior needle of the double ended needle. Accordingly, the combination of device 50 and receptacle 10 provides apparatus which will completely safeguard a clinician from contact with a double ended needle during the time subsequent to a venipuncture procedure to final disposal of the double ended needle.

Single ended needles attached to hypodermic needles have similar ribbed hubs. Accordingly, the present invention can be used to disengage such needles from their syringes.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. A disposal for receiving double ended needles, said disposal comprising in combination:
   a) a receptacle for housing the needles;
   b) a means disposed in said receptacle for receiving the anterior end of a blood collection tube holder and for accommodating rotation of the holder about its longitudinal axis, which holder includes a boss for threadedly engaging a ribbed hub disposed upon the double ended needle, said receiving means including means for supporting at least a part of the anterior end of the blood collection tube holder;
   c) a post for preventing rotation of the hub about the longitudinal axis of the needle by interferingly engaging a rib of the hub upon attempted rotation of the hub during rotation of the holder and for threadedly disengaging the hub from the holder during rotation of the holder;
   d) said receiving means including means for preventing lateral displacement of said holder to effect engagement of the hub with said post;
   e) an aperture disposed in said receiving means for accommodating passage of the needle upon threaded disengagement of the needle from the holder resulting from rotation of the holder relative to the hub; and
   f) means for urging disengagement of the hub to assist passage of the needle through said aperture.

2. The apparatus as set forth in claim 1 wherein said post includes an upper end and a ramp disposed at said upper end.

3. The apparatus as set forth in claim 1 wherein said supporting means includes a segment of an annular surface.

4. The apparatus as set forth in claim 1 wherein said receiving means includes a recess.

5. A disposal for receiving double ended needles, said disposal comprising in combination:
   a) a receptacle for housing the needles;
   b) a means disposed in said receptacle for receiving the anterior end of a blood collection tube holder and for accommodation rotation of the holder about its longitudinal axis, which holder includes a boss for threadedly engaging a ribbed hub disposed upon the double ended needle, said receiving means including means for supporting at least a part of the anterior end of the blood collection tube holder, said receiving means including a recess;
   c) a post for preventing rotation of the hub about the longitudinal axis of the needle by interferingly engaging a rib of the hub upon attempted rotation of the hub;
   d) an aperture disposed in said receiving means for accommodating passage of the needle upon threaded disengagement of the needle from the holder resulting from rotation of the holder relative to the hub; and
   e) a pair of diametrically opposed leaf springs disposed is said recess for urging disengagement of the needle from the holder after rotation of the holder relative to the needle.

6. The apparatus as set forth in claim 5 wherein each of said leaf springs includes a lip for engaging the hub to prevent rise of the needle upon withdrawal of the holder from said recess.

7. The apparatus as set forth in claim 4 wherein said recess includes a side wall and wherein said post extends radially inwardly from said side wall.

8. A disposal for receiving a double ended needle having a ribbed hub threadedly engaged with a blood collection tube holder, which holder is translatable within a guard having a collar disposed at the anterior end for receiving the hub, said disposal comprising in combination:
   a) a receptacle for housing the needle;
   b) means for supporting the anterior end of the collar with respect to said receptacle;
   c) a post extending into the guard for preventing rotation of the hub about the longitudinal axis of the needle by interferingly engaging a rib of the hub upon attempted rotation of the hub; and
   d) means for accommodating passage of the needle into said receptacle upon threaded disengagement of the needle from the holder resulting from rotation of the guard relative to the hub.

9. The apparatus as set forth in claim 8 wherein said post includes an upper end and a ramp disposed at said upper end.

10. The apparatus as set forth in claim 8 including means for urging separation between the needle and the holder after threaded disengagement therebetween.

11. The apparatus as set forth in claim 10 wherein said urging means comprises at least one leaf spring.

12. The apparatus as set forth in claim 11 wherein each of said leaf springs includes a lip for engaging the hub to prevent rise of the needle upon withdrawal of the holder.

13. The apparatus as set forth in claim 8 including a recess for receiving the collar and wherein said receptacle includes a top surface and wherein said supporting means comprises said top surface for supporting the holder.

14. The apparatus as set forth in claim 8 including a skirt depending from said top for defining said recess.

15. The apparatus as set forth in claim 14 including a shelf extending radially inwardly from said skirt.

16. The apparatus as set forth in claim 15 including a semicylindrical flange extending upwardly from said shelf to define a segment of an annular slot disposed between said semicylindrical flange and said skirt for receiving the collar.

17. The apparatus as set forth in claim 16 wherein said post extends radially inwardly of said semicylindrical flange.

18. A disposal for receiving double ended needles, said method comprising the steps of:
   a) providing a receptacle for housing the needles;
   b) receiving the anterior end of a blood collection tube holder in a recess associated with the receptacle, which recess accommodates rotation of the holder about its longitudinal axis and supports at least a part of the anterior end of the holder, the holder including a boss at the anterior end for threadedly engaging a ribbed hub disposed upon the needle;
   c) engaging a rib of the ribbed hub with a post disposed in the recess to prevent rotation of the hub about the longitudinal axis of the needle commensurate with rotation of the holder and thereby threadedly disengaging the hub from the holder during rotation of the holder;
   d) preventing lateral displacement of the holder to effect engagement of the hub with the post;
   e) passing the needles through an aperture disposed in the recess and into the receptacle upon threaded disengagement of the needle from the holder resulting from rotation of the holder relative to the hub and withdrawal of the holder; and
   f) urging disengagement of the hub to assist passage of the needle through the aperture.

19. The method as set forth in claim 18 including the step of restraining rise of the needle upon withdrawal of the holder.

20. A disposal for disposing double ended needles having a ribbed hub threadedly engaged with a blood collection tube holder translatable within a guard having a collar disposed at the anterior end for receiving and radially encircling the hub, said method comprising the steps of:
   a) providing a receptacle for housing the needles;
   b) receiving the collar of the guard in a recess of the receptacle;
   supporting the anterior end of the collar within the recess;
   d) engaging a rib of the hub with a post disposed in the recess to prevent rotation of the hub about the longitudinal axis of the needle; and
   e) passing the needle through a passageway and into the receptacle upon threaded disengagement of the needle from the holder resulting from rotation of the holder relative to the hub.

21. The method as set forth in claim 20 including the step of restraining rise of the needle upon withdrawal of the holder.

* * * * *